United States Patent [19]
Nay et al.

[11] Patent Number: 4,567,160
[45] Date of Patent: Jan. 28, 1986

[54] CATALYST COMPOSITION FOR THE PRODUCTION OF ALCOHOLS FROM SYNTHESIS GAS

[75] Inventors: Barry Nay, Woking; David G. Stewart, Epsom, both of England

[73] Assignee: The British Petroleum Company p.l.c., London, England

[21] Appl. No.: 510,882

[22] Filed: Jul. 5, 1983

[30] Foreign Application Priority Data

Jul. 9, 1982 [GB] United Kingdom ............... 8220083

[51] Int. Cl.$^4$ .................. B01J 23/58; B01J 23/72; B01J 23/89
[52] U.S. Cl. ..................... 502/326; 502/327; 502/329; 502/330; 502/331
[58] Field of Search ............ 502/326, 327, 329, 330, 502/331; 518/713, 715, 717, 718

[56] References Cited

U.S. PATENT DOCUMENTS 4,122,110 10/1978 Sugier et al. ............... 502/306 X
4,280,930 7/1981 Antos ........................... 502/326 X
4,291,126 9/1981 Sugier et al. ............... 518/713

Primary Examiner—W. J. Shine
Attorney, Agent, or Firm—Brooks Haidt Haffner & Delahunty

[57] ABSTRACT

A catalyst composition suitable for use in the production of alcohols from synthesis gas comprises as essential elements:
(a) cobalt
(b) one or more of copper, silver, gallium, zirconium, zinc and thorium
(c) one or more of palladium, platinum and nickel, and
(d) one or more alkali metals, in the atomic ratio of component (a): component (b): component (c) of 100:1 to 400:1 to 500, the alkali metal or metals forming up to 5% by weight of the composition. A suitable catalyst composition has the empirical formula:

$$(a)_{100} (b)_{1 \text{ to } 400} (c)_{1 \text{ to } 500} (d)_x O_y$$

wherein (a), (b), (c) and (d) are as above, the value of x is such that (d) forms up to 5% by weight of the composition and y is a number such that the valence requirements of the other elements for oxygen is satisfied.

3 Claims, No Drawings

CATALYST COMPOSITION FOR THE PRODUCTION OF ALCOHOLS FROM SYNTHESIS GAS

The present invention relates to a catalyst composition suitable for use in a process for the production of alcohols, in particular saturated straight-chain primary alcohols, from synthesis gas and to its use in such a process.

Two main types of process have been proposed for preparing alcohols from gaseous mixtures comprising carbon monoxide and hydrogen (synthesis gas). One of these is the modified Fischer Tropsch process which involves alkali metal-containing iron catalysts. Generally, this process suffers from poor selectivity and low productivity. The other process is the isobutyl synthesis as used in Europe between 1935 and 1945. This process is analogous to the methanol synthesis process and utilises a similar catalyst, ie zinc chromite, modified by addition of an alkali metal salt, at high temperatures (380 to 450° C.) and high pressures (300 to 400 bars). Typically the main products from this reaction comprise methanol (50%), ethanol (20–40%), n-propanol and higher alcohols which are predominantly non-linear primary and secondary alcohols. For both these processes it has been proposed in the prior art to incorporate in the catalyst a wide variety of metals.

U.S. Pat. No. 4,122,110 claims a process for manufacturing linear saturated primary alcohols, by reacting carbon monoxide with hydrogen at a pressure between 20 and 250 bars and a temperature between 150 and 400° C., in the presence of a catalyst, characterised in that the catalyst contains at least 4 essential elements:
(a) copper,
(b) cobalt,
(c) at least one element M selected from chromium, iron, vanadium and manganese, and
(d) at least one alkali metal A, in the following atomic proportions: $Cu_xCo_yM_zA_v$ where x is from 0.1 to 1, y from 0.1 to 1, z from 0.2 to 1 and v from 0.001 to 0.25 times the sum $(x+y+z)$.

By comparison with the aforesaid prior art processes it is claimed in U.S. Pat. No. 4,122,110 that the selectivity to alcohols is high (it may be higher than 95%, particularly when using the preferred method for manufacturing the catalyst); practically no hydrocarbons, particularly methane are formed; the selectivity to linear saturated primary alcohols of $C_2$ or more is often higher than 70% by weight; the productivity is great, higher than 100 kg of $C_2$+alcohols per cubic meter of catalyst per hour; and the operating conditions are milder.

According to the present invention there is provided a catalyst composition suitable for use in a process for the production of alcohols from synthesis gas which composition comprises as essential elements:
(a) cobalt,
(b) one or more of copper, silver, gallium, zirconium, zinc and thorium,
(c) one or more of palladium, platinum and nickel, and
(d) one or more alkali metals,
in the atomic ratio of component (a): component (b): component (c) of 100:1 to 400:1 to 500, the alkali metal or metals forming up to 5% by weight of the composition.

Whilst the precise form of the elements during use in a process for the production of alcohols from synthesis gas is not entirely known, they are thought to be in the form of their oxides, though it is possible that certain of the elements may be present in elemental form. It is known, however, that active catalytic compositions comprise the elements in the form of their oxides or in the form of salts which are decomposable by heat to oxides, such as carbonates, sulphates, nitrates or carboxylates.

A suitable composition has the empirical formula:

$$(a)_{100}(b)_{1\ to\ 400}(c)_{1\ to\ 500}(d)_xO_y$$

wherein
(a) is cobalt,
(b) is one or more of copper, silver, gallium, zirconium, zinc and thorium,
(c) is one or more of palladium, platinum and nickel, and
(d) is one or more of alkali metals
and wherein the value of x is such that (d) forms up to 5% by weight of the composition and y is a number such that the valence requirements of the other elements for oxygen is satisfied.

A particularly suitable composition comprises $Co.Cu.Pd_{0.05}K_xO_y$.

The composition may be prepared by a variety of different methods. Thus it may be prepared by simply admixing the individual oxides, or by precipitating the oxides either individually or collectively, or by impregnating an oxide with a solution or solutions of other oxides. Alternatively, instead of the oxides, heat decomposable salts may be used in any of the aforesaid methods for preparing the composition and the composition heated thereafter at a temperature above their decomposition temperatures.

Shaping may be affected by any conventional technique, for example by tabletting or extrusion, or by pill-forming, optionally incorporating also binders such as alumina, magnesia and aluminous refractory cements. The preferred aluminous cements contain from 40 to 85% b.w. $Al_2O_3$ and 15 to 30% b.w. CaO with optionally small amounts of other components.

In another aspect, the invention provides a process for the production of alcohols which process comprises reacting carbon monoxide with hydrogen at elevated temperature and pressure in the presence as catalyst of a composition as described hereinbefore.

Before use as a catalyst it is particularly preferred to heat the composition in a reducing atmosphere, eg in a stream of a reducing gas. Typically, this may be effected by heating at a temperature of about 350° C. in a stream of hydrogen for a period of 18 hours. Following reduction, and until its use as a catalyst in the process of the invention, the composition must be stored in a substantially oxygen-free atmosphere.

Mixtures of the gases carbon monoxide and hydrogen are abundantly available in the form of synthesis gas. Methods for preparing synthesis gas are well known in the art and usually involve the partial oxidation of a carbonaceous substance, eg coal. Alternatively, synthesis gas may be prepared, for example, by the catalytic steam reforming a methane. Although it is preferred to use substantially pure synthesis gas, the presence of such impurities as carbon dioxide and nitrogen can be tolerated. On the other hand, impurities which have a deleterious effect on the reaction should be avoided. The molar ratio of carbon monoxide to hydrogen may suitably be in the range 5:1 to 1:5. In general, a high proportion of hydrogen favours the formation of hydrocarbons whilst a low proportion of hydrogen favours the formation of oxygenated hydrocarbons. Methods for adjusting the molar ratio of hydrogen to carbon monoxide by the so-called shift reaction are well known in the art.

The elevated temperature may suitably be in the range from 200 to 450° C. and the elevated pressure may suitably be in the range from 25 to 300 bars.

Although the process may be carried out batchwise, it is preferably operated in a continuous manner. Suitably, the contact time, defined as:

$$\frac{\text{Volume of catalyst in milliliters}}{\text{Total volume of gas (in milliliters/second at } NTP\text{)}}$$

may be in the range from 1 to 30 seconds.

The catalyst may be employed in the form of a fixed or a fluidised bed.

The liquid product principally comprises saturated straight-chain primary alcohols such as methanol, ethanol, propanol and butanol.

The invention will now be further illustrated by reference to the following Examples.

EXAMPLE

Preparation of Cu Co $Pd_{0.05}$ $K_x$ $O_y$ Catalyst $Cu(NO_3)_2 3H_2O$ (48.3 g) and $Co(NO_3)_2 6H_2O$ (58.2 g) were dissolved in deionised water (200 ml). To this was added a solution of palladium acetate (1.48 g) dissolved in conc nitric acid (10 ml). This mixture was then added to a solution of potassium carbonate (68.1 g) in deionised water (300 ml) maintained at 60° C. The pH was adjusted to about 7.0 by the addition of potassium carbonate, and the resulting precipitate filtered, washed with deionised water (3×500 ml) and dried. The resulting dark solid was heated in air at 400° C. for 4 hours, cooled and made into pellets. The pellets were broken down and were sieved to give 16 to 20 mesh granules. The catalyst was reduced at 350° C. under a slow flow of hydrogen for 18 hours before use.

Use of catalyst in a process for the production of alcohols from synthesis gas

A mixture of carbon monoxide and hydrogen was contacted with the Cu Co $Pd_{0.05}$ $K_x$ $O_y$ catalyst prepared in the manner hereinbefore described. The reaction conditions were as follows:

Run pressure=50 bar
Run temperature=348° C.
Catalyst=15 ml
Feed CO:$H_2$ molar ratio=1:1
Contact time=2.21 sec Under these operating conditions the carbon monoxide conversion was 19.4% and a liquid organic product was obtained with the following composition (% w/w):
Methanol—30
Ethanol—49
n-Propanol—14
Butanol—7

The main byproducts were methane and carbon dioxide.

EXAMPLE 2

Preparation of Cu Co $Pd_{0.05}$ $K_x$ $O_y$ wherein x is approximately 1.5% wt/wt and y is a number such that the valence requirements of the other elements for oxygen is satisfied.

$Cu(NO_3)_2.3H_2O$ (48.3 g) and $Co(NO_3)_2.6H_2O$ (58.2 g) were dissolved in separate breakers of water and then combined to give one solution. To this was added a solution of palladium chloride (1.54 g) dissolved in conc. nitric acid (10 ml). The solution was heated to about 90° C. and a warm solution of potassium carbonate (68.1 g) added slowly with stirring until pH9.0 was obtained. The pH was adjusted to pH7.0 by the careful addition of 20% nitric acid. The mixture was cooled and the precipitate filtered off. The precipitate was washed by slurrying several times with deionised water and over dried at about 120° C. overnight. The powder was heated at 275° C. for 4 hours and finally at about 400° C. for 16 hours to decompose any remaining nitrates or carbonates. The hard cake was broken up and sieved to 8-16 BSS granules. The catalyst was reduced by contact at 200° C. with nitrogen initially and gradually changing over a period of 7 hours to hydrogen (100%), followed by hydrogen (100%) at 200° C. for 16 hours.

Use of catalyst in a process for the production of alcohols from synthesis gas

A mixture of carbon monoxide and hydrogen was contacted with the catalyst prepared in the aforesaid manner. The reaction conditions were as follows:

Run pressure=50 bars
Run temperature=335° C.
Catalyst=15 ml
Feed CO:$H_2$ molar ratio=1:1
G.H.S.V.=8373$h^{-1}$ Under these operating conditions the carbon monoxide conversion was 21.5% and a liquid organic product was obtained with the following composition (%w/w):
Methanol—25.1
Ethanol—35.1
Propanol—20.2
Butanol—19.6

We claim:

1. A catalyst composition suitable for use in a process for the production of alcohols from synthesis gas which composition consists essentially of:
   (a) cobalt,
   (b) one or more of copper, silver, gallium, zirconium, zinc and thorium,
   (c) one or more of palladium, platinum and nickel, and
   (d) one or more alkali metals, in the atomic ratio of component (a): component (b); component (c) of 100:1 to 400:1 to 500, the alkali metal or metals forming up to 5% by weight of the composition and wherein said essential elements are present in the form of their oxides or in the form of salts which are decomposable by heat to oxides.

2. A catalyst composition according to claim 1 having the empirical formula:

$$(a)_{100}(b)_{1\ to\ 400}(c)_{1\ to\ 500}(d)_x O_y$$

wherein
   (a) is cobalt
   (b) is one or more of copper, silver, gallium, zirconium, zinc and thorium,
   (c) is one or more of palladium, platinum and nickel, and,
   (d) is one or more alkali metals and wherein the value of x is such that (d) form up to 5% by weight of the composition and y is a number such that the valence requirements of the other elements for oxygen is satisfied.

3. A catalyst composition according to claim 2 consisting essentially of $Co.Cu.Pd_{0.05}K_xO_y$.

* * * * *

UNITED STATES PATENT AND TRADEMARK OFFICE
CERTIFICATE OF CORRECTION

PATENT NO. : 4,567,160
DATED : January 28, 1986
INVENTOR(S) : BARRY NAY and DAVID G. STEWART It is certified that error appears in the above-identified patent and that said Letters Patent are hereby corrected as shown below:

Col. 2, line 19, "of alkali metals" should read --alkali metals--

Col. 2, line 62, "a methane" should read --of methane--

Col. 3, line 67, "breakers" should read --beakers--

Col. 4, line 9, "over dried" should read --oven dried--

Signed and Sealed this

Fifteenth Day of April 1986

[SEAL]

Attest:

DONALD J. QUIGG

Attesting Officer

Commissioner of Patents and Trademarks